United States Patent [19]
Spinks et al.

[11] Patent Number: 5,892,162
[45] Date of Patent: Apr. 6, 1999

[54] APPARATUS AND METHOD FOR INSPECTION OF PIPES AND TUBES USING GUIDED WAVE PROBE

[75] Inventors: Robert L. Spinks; Joseph W. Brophy; Ronald H. Peterson, all of San Antonio, Tex.

[73] Assignee: Southwest Research Institute

[21] Appl. No.: 972,379

[22] Filed: Nov. 18, 1997

[51] Int. Cl.$^6$ .......................... G01M 19/00; G01M 3/08; G01N 29/00; G01H 3/00
[52] U.S. Cl. .......................... 73/865.8; 73/405 A; 73/591; 73/592; 73/661
[58] Field of Search .......................... 73/40.5 R, 40.5 A, 73/591, 592, 865.8, 661

[56] References Cited

U.S. PATENT DOCUMENTS

| | | | |
|---|---|---|---|
| 4,265,025 | 5/1981 | Finlayson et al. | 33/178 F |
| 4,342,225 | 8/1982 | Jandera et al. | 73/865.8 |
| 4,909,080 | 3/1990 | Kikuta et al. | 73/290 V |
| 5,379,643 | 1/1995 | Taylor | 73/661 |
| 5,686,674 | 11/1997 | Lowry et al. | 73/865.8 |

FOREIGN PATENT DOCUMENTS

| | | | |
|---|---|---|---|
| 0872742 | 10/1981 | U.S.S.R. | 73/40.5 A |
| 0926547 | 5/1982 | U.S.S.R. | 73/40.5 A |

Primary Examiner—Hezron Williams
Assistant Examiner—Chad Soliz
Attorney, Agent, or Firm—Kammer & Huff, PLLC

[57] ABSTRACT

An apparatus and method for directing ultrasonic and magnetostrictively generated mechanical waves from an exterior point to an interior point within a small diameter tube, pipe, or cylindrical structure. The present invention incorporates an external mechanism for generating waves in a cylindrical waveguide tube gun of a size small enough for insertion into the target tube and configured so as to maintain mechanical contact with an inside diameter of the target tube. Standard ultrasonic wave generating devices or magnetostrictive/mechanical wave generating coils are positioned on the waveguide external to the target tube and generate appropriate mechanical waves through the waveguide to a point interior to the target tube. A mechanical interface between the waveguide and the inside diameter surface of the tube is positioned and provided at a point within the target tube to transfer both the interrogating waves and the received return signal waves between the target tube and the waveguide. Appropriate sensor devices for ultrasonic and/or magnetostrictive/mechanical waves are positioned to receive the returned signals and interpret the impedance mismatches that indicate flaws, supports and geometric variations in the tubular wall. Appropriate signal reception, amplification, and filtration elements are positioned to convert the received signal into a signal voltage suitable for display and processing.

7 Claims, 3 Drawing Sheets ary of the Invention

APPARATUS AND METHOD FOR INSPECTION OF PIPES AND TUBES USING GUIDED WAVE PROBE

BACKGROUND OF THE INVENTION

1. Field of the Invention

The present invention relates generally to devices and methods for the non-destructive evaluation of the condition of tubes, pipes, cylindrical shells and the like. The present invention relates more specifically to a probe structure and method for conducting ultrasonic, magnetostrictive, and other similar wave propagated evaluations of tubes, pipes, cylindrical structures and the like from the interior of such structures with limited access.

2. Description of the Related Art

Many industrial structures, frames, conduits, flow columns and the like, are constructed in cylindrical configurations that are often difficult to access. Inspecting small diameter tubing and pipes for defects and the effects of corrosion is important but extremely difficult due to the geometrical constraints of the available working space. Efforts to inspect such tubes and pipes from the outside diameter (OD) is restricted because of the frequent use of supporting structures that are attached to the external surface of the pipes or tubes. Ideally, the easiest longitudinal access to such tubular pipe structures is from the inside since most frequently the interior walls are free from limiting support structures. Unfortunately, the aforementioned constraints of the typical cross-sectional geometries of tubing, pipes and the like, prohibit the introduction of the necessary probes and electronics into the internal diameter (ID) of the target tubing.

Once the interior diameter of a target tube is accessed, ultrasonic waves and magnetostrictive based mechanical waves can be used to inspect the tube wall for defects and/or wall thinning. The problem in most every instance is actually injecting the interrogating waves into the interior surface of the tube walls. In addition, the types of waves most suitable for inspection of the length of a target tube are those that propagate longitudinally through the walls in a uniform and symmetrical fashion. In other words, insertion of interrogating waves at a single point in the cylindrical wall of a tube would generally introduce conflicting wave patterns that complicate the detection and analysis of signal returns from anomalies. It is preferable to inject interrogating waves in uniform and symmetrical form so as to simplify the reception, interpretation, and analysis of a return signal.

SUMMARY OF THE INVENTION

It is therefore an object of the present invention to provide an apparatus and method for the inspection of small diameter tubing, pipes, and cylindrical structures for defects and the effects of corrosion from the inside diameter of the structures.

It is an object of the present invention to permit the inspection of tubes, pipes, and cylindrical structures from an inside diameter, by providing a means for generating guided waves external to the tube to a location adjacent and in mechanical contact with the inside diameter of the tube for the purpose of injecting the interrogating waves longitudinally into the structure.

It is a further object of the present invention to provide a means for inspecting small diameter tubing for defects and the effects of corrosion through the use of ultrasonics and/or magnetostrictively generated waves by generating such waves external to the tube and providing a waveguide for transmitting the generated waves to the interior diameter of the tube.

It is a further object of the present invention to provide an apparatus and method for the inspection of small diameter tubing for defects and the effects of corrosion by generating and injecting interrogating waves in a uniform and symmetrical manner so as to simplify the reception, interpretation and analysis of a return signal that propagates back to the sensors of the present invention.

It is a further object of the present invention to provide a system for inspecting small diameter tubing for defects and the effects of corrosion by utilizing ultrasonic wave generating systems and coupling such ultrasonic wave generating systems to the interior of the target tubing by means of an appropriately configured waveguide.

In fulfillment of these and other objectives, the present invention provides an apparatus and method for directing ultrasonic and magnetostrictively generated mechanical waves from an exterior point to an interior point within a small diameter tube, pipe, or cylindrical structure. The present invention incorporates an external mechanism for generating waves in a cylindrical waveguide tube gun of a size small enough for insertion into the target tube and configured so as to have a means for maintaining mechanical contact with an inside diameter of the target tube. Standard ultrasonic wave generating devices or magnetostrictive/mechanical wave generating coils are positioned on the waveguide external to the target tube and generate appropriate mechanical waves through the waveguide to an interior location in the target tube. A mechanical interface between the waveguide and the inside diameter surface of the tube is positioned and provided at a point within the target tube to transfer the interrogating waves and the received return signal waves between the target tube and the waveguide. Appropriate sensor devices for ultrasonic and/or magnetostrictive/mechanical waves are positioned to receive the returned signals and interpret the impedance mismatches that indicate flaws, supports and geometric variations in the tubular wall. Appropriate signal reception, amplification, and filtration elements are positioned to convert the received signal into a signal voltage suitable for display and processing. Other objects of the present invention will become apparent to those skilled in the art after the review of the following specifications and the appended drawings.

DESCRIPTION OF THE PREFERRED EMBODIMENT

Figure 1:
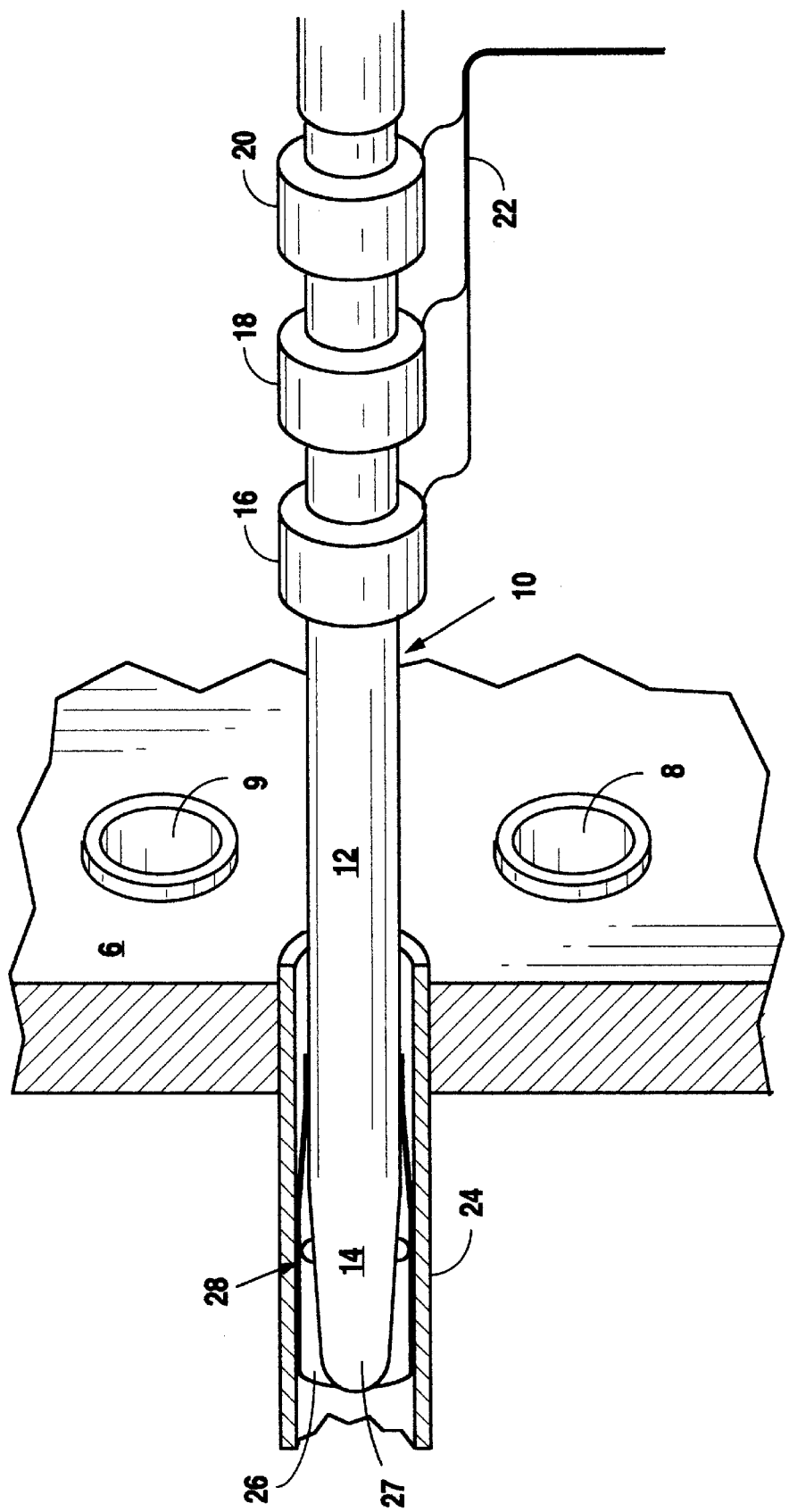
FIG. 1 is a partial cross-sectional view showing in perspective the primary components of the system of the present invention.

Reference is made first to FIG. 1 for a detailed description of the waveguide probe instrument of the present invention.

FIG. 1 is a partial cross-section, perspective view of one possible application of the instrument of the present invention in use for inspection of an array of heat exchanger tubes as might be found in boilers, nuclear reactors, and other power-generating facilities. The present invention is especially suitable for the inspection of a large array of tubes whose interiors are accessible at least one end and which are closely spaced together such as in a heat exchange panel or cylinder.

FIG. 1 discloses waveguide instrument (10) in a perspective view as it may be inserted into the interior diameter of one tube in a heat exchanger structure shown in cross-section. The primary component of waveguide (10) is tubular probe (12) which serves to carry and transmit both the interrogating waves and the return signal waves between the instrumentation of the invention and the target tubing. At the working end of tube probe (12) is mechanical interface structure (14) suitable for conducting ultrasonic or other mechanical waves from tube probe (12) into the target tubing. In the preferred embodiment of the present invention, mechanical interface (14) comprises a plurality of expandable wings (27) that permit mechanical contact with the interior surface of the target tube as is described in more detail below.

At an opposite end of tubular probe (12), a plurality of magnetostrictive coils (16, 18 and 20) surround tubular probe (12) so as to be appropriately positioned to generate mechanical waves within probe (12). Coils (16, 18 and 20) are controlled by way of signal cable (22) which serves the dual purpose of delivering a signal which generates the interrogating mechanical wave and receiving signals associated with a return wave.

Tubular probe (12) is inserted into target tube (24) held in position in a tube sheet (6) along with other adjacent tubes (8) and (9). Tubular probe (12) has an outer diameter slightly less than that of the inner diameter of target tube (24). This permits the easy insertion of tubular probe (12) into target tube (24) prior to the expansion of the mechanical interface (14) within target tube (24). Once inserted, the plurality of expansion wings (27) are forced outward by drawing in mechanical plug (26) as shown in FIG. 1. The mechanical interface section of tubular probe (12) can be as simple as an array of split wings (27) formed from the cylindrical shell of the tubular structure which are expanded with the insertion of a plug (26) having a diameter slightly larger than the inside diameter of tubular probe (12). Plug (26) can be drawn into tubular probe (12) in the manner described in more detail with respect to FIG. 4.

It is anticipated that there are a number of mechanisms whereby the cylindrical shell structure of tubular probe (12) can be forced into mechanical contact with the interior surface of target tube (24). The example shown in FIG. 1 is one of a number of mechanisms suitable for temporarily expanding the outside diameter of tubular probe (12) to match the inner diameter of target tube (24). In any case, mechanical expansion plug (26) serves to create mechanical contact between a large surface area (28) on the external surface of tubular probe (12) for the transmission of both incident and return waves between tubular probe (12) and target tube (24).

Figure 2:
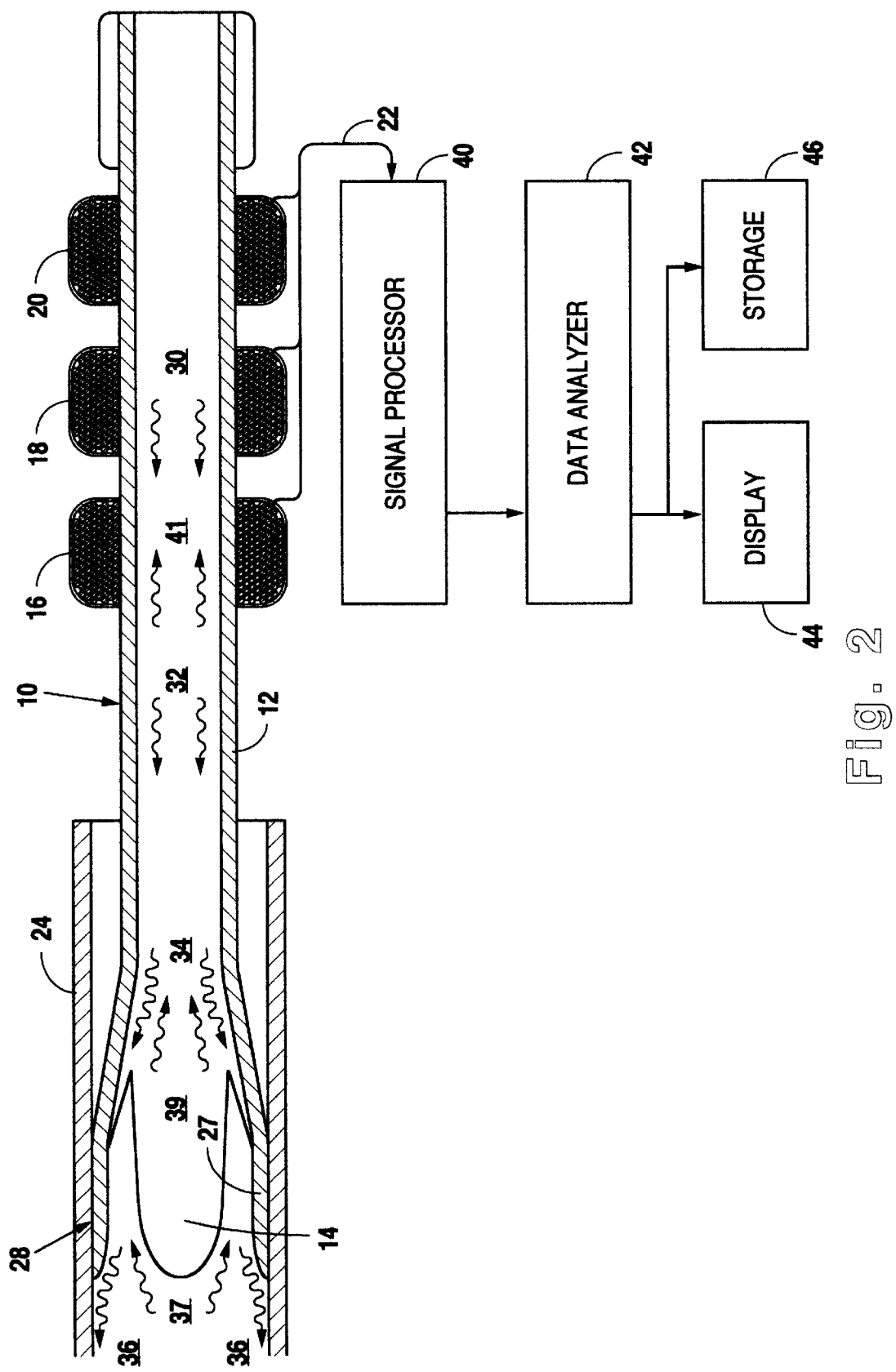
FIG. 2 is schematic diagram showing in cross-section the transfer and propagation of waves within the elements of the present invention.

Reference is now made to FIG. 2 for a detailed description of the electronic components of the present invention and the overall function of the device in identifying anomalies in the cylindrical structure of the target tubing. Tubular probe (12) is shown in cross-section in FIG. 2 with the expansion plug removed for clarity. Areas of contact (28) permit the transmission of various mechanical waves back and forth between tubular probe (12) and target tube (24). In the examples shown in FIG. 2, a plurality of magnetostrictive coils or piezoelectric elements (16), (18) and (20) are positioned in a manner that permits the generation of mechanical waves with a first transmission coil, (18) for example, and the reception of return signal waves with a receiving coil, (16) for example. Coil (18) can be used to establish a base-line bias magnetic field to facilitate the signal reception and linearity for the return signals and as a spatial filter when used with coil (16) and spaced for differential reception.

Signal generator/processor (40) serves to drive transmitter coil (20) to initiate a magnetostrictive pulse to generate a mechanical wave to travel in tubular probe (12). An alternate method using piezoelectric elements to generate the mechanical wave may be used. This mechanical wave (30) passes longitudinally down the cylindrical structure of tubular probe (12) to a point (32) where it enters target tubing (24). Mechanical waves (34) follow the configuration of the walls of tubular probe (12) through the mechanical interface area towards contact with the interior walls of target tubing (24). The mechanical contact (28) between tubular probe (12) and target tubing (24) permits the transmission of incident mechanical waves (36) into target tubing (24) and the transmission of reflected mechanical waves (37) back from target tubing (24) into tubular probe (12). It is anticipated that the combination of sufficient force created by mechanical plug (26) (not shown in FIG. 2) and the possible utilization of a coupling fluid or gel will facilitate the transmission of waves back and forth across the mechanical interface.

A return signal, comprised of mechanical wave (37) whose characteristics would be indicative of anomalies in the tubing, would likewise be transmitted from target tubing (24) through the mechanical interface to tubular probe (12). The return signal, comprised of mechanical waves (39), follows the configuration of the walls of tubular probe (12) to a point (41) where they may be detected by receiver coil (16). Receiver coil (16) translates the acoustic or mechanical waves back into electrical signals which are transmitted via line (22) to signal processor (40) where they are filtered and amplified. Signal processor (40) provides a clean signal to data analyzer (42) which may serve to both display the data graphically on display (44) and store the data for later review in data storage (46).

Figure 3:
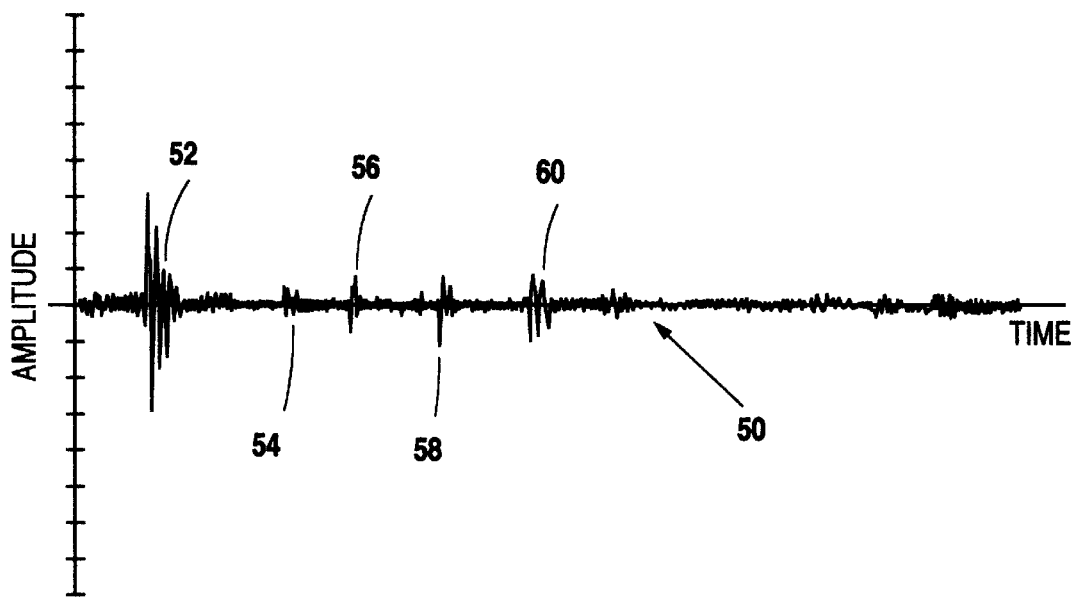
FIG. 3 is a graphical depiction of a return signal showing an ultrasonic amplitude signal received back utilizing the apparatus of the present invention.

Reference is now made to FIG. 3 for an example of the type of signal returned by the system of the present invention when utilized in conjunction with the transmission of either ultrasonic waves or magnetostrictively generated mechanical waves. Return signal (50) in the example shown in FIG. 3 is comprised of a number of identifiable characteristics that permit the interpretation and analysis of the material through which the wave has traveled. A knowledge of the mechanical structure of the interrogating probe and the characteristics of the interrogating wave permit an analysis of the characteristics of the target tubing through well known analytical methods associated with wave propagation, pattern recognition and so on. Following the example given above with respect to FIG. 2, a wave generated by a transmitting coil might first pass the receiving coil to provide wave peak (52) indicative of the incident interrogating wave form. A first return signal pulse (54) may be identified as being indicative of the mechanical interface between the tubular probe and the target tubing. Subsequent wave peaks (56) and (58) would be interpreted as anomalies such as cracks, pitting, or wall thinning areas within the target tube.

Finally, wave peak (60) could be interpreted as a reflected signal from a terminal end of the target tube. It is anticipated that the interpretation of the return signal such as that shown in FIG. 3 would be based upon recognizable patterns established with known target tube geometries and recognizable tube wall anomalies.

Figure 4:
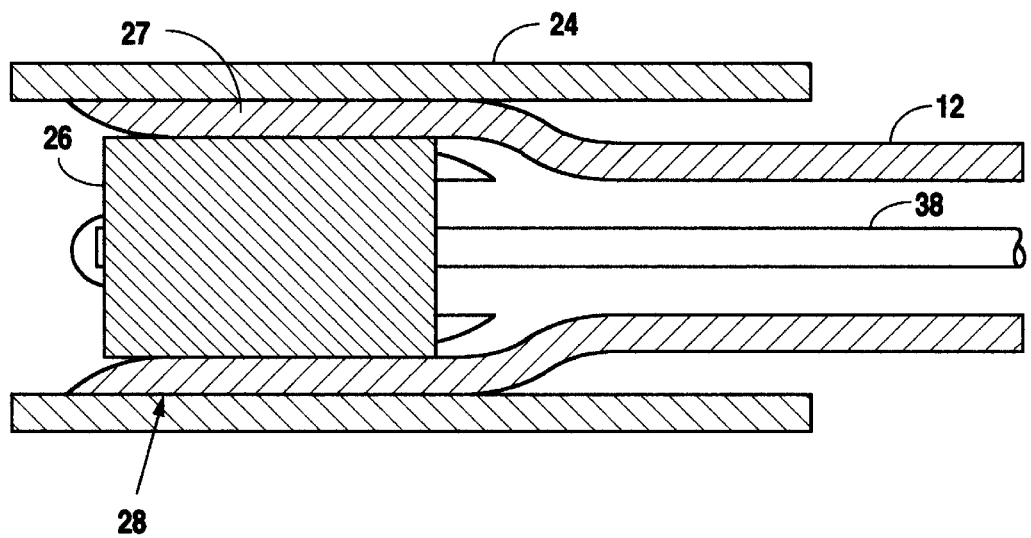
FIG. 4 is a detailed cross-sectional view showing the configuration of the mechanical plug used to ensure contact between the waveguide of the present invention and the target tubing.

Reference is now made to FIG. 4 for a detailed description of the mechanism whereby mechanical contact is maintained between an outside diameter of tubular probe (12) and the inside diameter of target tube (24). In this cross-sectional detail, mechanical plug (26) is shown in place forcing the walls of tubular probe (12) outward against the inside diameter of target tube (24). The geometry of mechanical plug (26) and the malleability or flexibility of the walls of tubular probe (12), together contribute to an amount of mechanical contact (28) between the probe and the target tube. A variety of mechanisms for drawing mechanical plug into tube probe (12) so as to force the walls outward can be utilized. One example shown in FIG. 4 is the use of an axial rod (38) attached to mechanical plug (26) which through a variety of means can be drawn into tubular probe (12) at an opposite end thereof to forcefully pull mechanical plug (26) inside tubular probe (12).

The advantages created by the structure of the present invention are such as to permit the rapid investigation of a large number of tubular structures such as might be found in an array of tubes held in a heat exchanger system. In situations where it is necessary to rapidly investigate such a large number of tubes, the present invention facilitates the insertion of an easily movable waveguide into each of the target tubes without the necessity of realigning and repositioning the electronics normally associated with ultrasonic or magnetostrictive sensing. Configured in the form of a hand-held gun, the probe of the present invention could be readily moved from one tube to another without disturbing or disrupting the electronics necessary to display, analyze and store the data acquired. Appropriate mechanisms for expanding and contracting the mechanical interface of the waveguide tube further facilitate the easy removal and insertion of the device into the large array of tubular pipes.

The present invention provides mechanical contact with the target tubing sufficient to permit the utilization of standard ultrasonic and magnetostrictive interrogation methods. In general, the structural geometry of the present invention could be utilized in conjunction with the variety of non-destructive evaluation methods that depend upon a mechanical coupling between the probe and a target object to be analyzed. The present invention finds particular application to cylindrical structures but the same principles involved could easily be utilized in longitudinal structures of a variety of cross-sections. Slight modifications to the structure of the probe itself could permit its use in conjunction with a variety of enclosed shell elements.

Although the present invention has been described in conjunction with a preferred embodiment and a number of alternative approaches to a variety of the elements in the invention have been described, it is anticipated that other applications of the present invention will be envisioned from a consideration of the preferred embodiment, the drawings attached, all of which fall under the scope of the claims that follow.

We claim:

1. An apparatus for inspecting small diameter tubes, pipes, and cylindrical shell structures for defects and the effects of corrosion, from the inside diameter of said cylindrical structures, comprising:

a cylindrical probe, said probe having an outside diameter less than an inside diameter of a target cylindrical structure, said cylindrical probe further comprising an expandable interface, said expandable interface positioned at a first end of said cylindrical probe and being movable from having an outside diameter less than an inside diameter of said target cylindrical structure, to a geometry having an outside diameter so as to provide mechanical contact between an outside surface of said cylindrical probe and an inside surface of said target cylindrical structure at a mechanical contact point;

means for generating mechanical waves at a second end of said cylindrical probe, said second end of said probe being external to said target cylindrical structure, said mechanical waves traveling from said second end of said cylindrical probe through said first end of said cylindrical probe at said mechanical contact point between said cylindrical probe and said target cylindrical structure, and into said target cylindrical structure;

means for receiving a return wave, said return wave being reflected from mechanical geometries and anomalies within said target cylindrical structure, wherein characteristics of said return wave are indicative of structural characteristics of said target cylindrical structure.

2. The apparatus of claim 1 further comprising a mechanical plug, said mechanical plug insertable into said first end of said cylindrical probe and serving to force an expansion of said expandable interface on said cylindrical probe so as to maintain said mechanical contact between said cylindrical probe and said target cylindrical structure.

3. The apparatus of claim 1, wherein said means for generating a mechanical wave within said cylindrical probe comprises an ultrasonic transducer.

4. The apparatus of claim 1, wherein said means for generating a mechanical wave within said cylindrical probe comprises at least one magnetostrictive coil.

5. The apparatus of claim 1, wherein said means for receiving said return signal comprises an ultrasonic transducer.

6. The apparatus of claim 1, wherein said means for receiving said return signal comprises a magnetostrictive coil.

7. The apparatus of claim 1, further comprising a signal processor/signal generator, a data analyzer, a data display, and a data storage device.

* * * * *